(12) United States Patent
Saito et al.

(10) Patent No.: US 10,866,331 B2
(45) Date of Patent: Dec. 15, 2020

(54) X-RAY INSPECTION APPARATUS

(71) Applicant: ANRITSU INFIVIS CO., LTD., Kanagawa (JP)

(72) Inventors: Naoya Saito, Kanagawa (JP); Itaru Miyazaki, Kanagawa (JP)

(73) Assignee: ANRITSU INFIVIS CO., LTD., Kanagawa (JP)

( * ) Notice: Subject to any disclaimer, the term of this patent is extended or adjusted under 35 U.S.C. 154(b) by 0 days.

(21) Appl. No.: 16/578,523

(22) Filed: Sep. 23, 2019

(65) Prior Publication Data

US 2020/0116877 A1 Apr. 16, 2020

(30) Foreign Application Priority Data

Oct. 12, 2018 (JP) .................................. 2018-193331

(51) Int. Cl.
*G01T 1/29* (2006.01)
*G01N 23/083* (2018.01)
*G21K 1/02* (2006.01)
*G01T 1/20* (2006.01)
*H05G 1/10* (2006.01)

(52) U.S. Cl.
CPC ......... *G01T 1/2964* (2013.01); *G01N 23/083* (2013.01); *G01T 1/2018* (2013.01); *G21K 1/02* (2013.01); *H05G 1/10* (2013.01)

(58) Field of Classification Search
CPC ... G01T 1/2964; G01T 1/2018; G01N 23/083; H05G 1/10; G21K 1/02; G01V 5/0016
See application file for complete search history.

(56) References Cited

U.S. PATENT DOCUMENTS

| 2007/0025506 A1* | 2/2007 | Hirose | G06T 7/0004 378/57 |
| 2008/0063148 A1* | 3/2008 | Kabumoto | G01N 23/083 378/177 |
| 2010/0002835 A1* | 1/2010 | Kabumoto | G01N 23/04 378/57 |
| 2013/0032728 A1* | 2/2013 | Matoba | G01N 23/083 250/394 |

(Continued)

FOREIGN PATENT DOCUMENTS

| JP | H04-329935 A | 11/1992 |
| JP | 2011-242374 A | 12/2011 |
| JP | 2018-146554 A | 9/2018 |

*Primary Examiner* — Courtney D Thomas
(74) *Attorney, Agent, or Firm* — Pearne & Gordon LLP

(57) ABSTRACT

Provided is an X-ray inspection apparatus that can inspect an object to be inspected with high sensitivity by using a multiple-stage X-ray sensor without widening a slit of a collimator, and can prevent the apparatus from becoming large-sized due to prevention of X-ray leakage. An X-ray inspection apparatus includes an X-ray irradiation portion having an X-ray tube generating an X-ray, an X-ray sensor having detection element arrays in a plurality of stages in a carrying direction, the detection element arrays each formed of a plurality of detection elements linearly arranged in a main scanning direction orthogonal to the carrying direction on a plane parallel to the carrying surface of an object to be inspected, a collimator restricting an X-ray irradiation region for the X-ray sensor, and an imaging condition input section that designates one or more detection element arrays to be used for inspection.

3 Claims, 4 Drawing Sheets

(56) References Cited

U.S. PATENT DOCUMENTS

2016/0041110 A1\* 2/2016 Matoba .................... G01T 7/08
378/54
2016/0252470 A1\* 9/2016 Momose .......... G01N 23/20075
378/36

\* cited by examiner

X-RAY INSPECTION APPARATUS

TECHNICAL FIELD

The present invention relates to an X-ray inspection apparatus that irradiates a carried object to be inspected with an X-ray, and inspects the object to be inspected on the basis of a transmission amount of the X-ray passing through the object to be inspected when the X-ray is applied.

BACKGROUND ART

An X-ray inspection apparatus is an apparatus that inspects objects to be inspected such as, raw meat, fish, processed food, and performs various inspections such as whether or not a foreign substance is contained, whether or not a seal part is defective, and whether or not there is a defective object on the basis of a transmission amount of an X-ray passing through the object to be inspected when the object to be inspected is irradiated with the X-ray.

In the X-ray inspection apparatus, in order to reduce an amount of an X-ray leaking out of the apparatus, an X-ray applied from an X-ray irradiation portion is narrowed by a slit of a collimator made of a thin groove-shaped member such that the X-ray is not diffused to a region other than an X-ray line sensor, and thus an X-ray irradiation region for the X-ray line sensor is restricted.

Detection of an X-ray in the X-ray line sensor is performed on an X-ray that passes through the slit of the collimator from a focal point (a point where electrons collide and the X-ray is generated) of an anode target of an X-ray tube. The X-ray sensor formed of multiple-stage X-ray detection element arrays is used to detect a foreign substance with high sensitivity while reducing power of an X-ray.

In this case, in order to facilitate positioning between the slit of the collimator and the X-ray sensor, it is necessary to widen the slit by giving a margin to a size of the slit.

As such a type of X-ray inspection apparatus of the related art, there are apparatuses disclosed in Patent Documents 1 to 3. In the apparatus disclosed in Patent Document 1, an image having high sharpness is obtained by adjusting a positional relationship between an X-ray tube and a collimator. In the apparatus disclosed in Patent Document 2, a time delayed integration (TDI) type X-ray sensor that can perform time delayed integration with a plurality of detection element arrays is provided, the number of stages of detection element arrays that are used to perform time delayed integration is set according to thickness information of an object to be inspected W, and thus inspection can be performed with high sensitivity at low X-ray power. In the apparatus disclosed in Patent Document 3, a position of at least one of an X-ray irradiation portion, an X-ray sensor, and a collimator is controlled according to the temperature of an X-ray tube such that an amount of a focal position movement of a focal temperature in position adjustment data corresponding to a temperature is canceled out.

RELATED ART DOCUMENT

Patent Document

[Patent Document 1] JP-A-4-329935
[Patent Document 2] JP-A-2011-242374
[Patent Document 3] JP-A-2018-146554

DISCLOSURE OF THE INVENTION

Problem that the Invention is to Solve

However, in the X-ray inspection apparatuses disclosed in Patent Documents 1 and 2, in a case where the slit of the collimator is wide, there is the need for countermeasures such as provision of more shield curtains on a carry-in port side and a carry-out port side by increasing an apparatus length in order to prevent an increase in a leakage amount of an X-ray from the apparatus, and thus there is a problem in that the entire apparatus becomes large-sized. In the X-ray inspection apparatus disclosed in Patent Document 3, position adjustment may be performed to cancel out a so-called temperature drift, but a slit is required to be widened in order to facilitate the position adjustment, and thus there is room for examination.

Therefore, the present invention has been made to solve the problems of the related art, and an object thereof is to provide an X-ray inspection apparatus that can inspect an object to be inspected with high sensitivity by using a X-ray sensor without widening a slit of a collimator, and can prevent the apparatus from becoming large-sized due to prevention of X-ray leakage.

Means for Solving the Problem

According to the present invention, there is provided an X-ray inspection apparatus that irradiates a carried object to be inspected with an X-ray, and inspects the object to be inspected on the basis of a transmission amount of the X-ray transmitted through the object to be inspected, the X-ray inspection apparatus including an X-ray irradiation portion that has an X-ray tube generating the X-ray; an X-ray sensor that has detection element arrays in a plurality of stages in a carrying direction, the detection element arrays each formed of a plurality of detection elements linearly arranged in a main scanning direction orthogonal to the carrying direction on a plane parallel to a carrying surface of the object to be inspected and detecting the X-ray; a collimator that restricts an irradiation region of the X-ray for the X-ray sensor; and a designation section that designates one or more detection element arrays to be used for inspection in the irradiation region restricted by the collimator.

With this configuration, therefore, an operator can designate a detection element array detecting an X-ray with high efficiency in an irradiation region on the basis of, for example, a table for defining a correlation between a position of the collimator and an X-ray irradiation region. As a result, it is possible to inspect an object to be inspected with high sensitivity with the multiple-stage X-ray sensor without widening the slit of the collimator, and to prevent the apparatus from becoming large-sized due to prevention of X-ray leakage.

The X-ray inspection apparatus according to the present invention further includes a display section that displays a detection amount of X-rays detected by the detection element arrays in the plurality of stages.

With this configuration, an operator can judge which detection element array is detecting an X-ray with high efficiency by referring to displayed X-ray detection amounts, and can thus designate the detection element array as one or more detection element arrays to be used for inspection.

The X-ray inspection apparatus according to the present invention further includes a determination section that determines the one or more detection element arrays to be used for the inspection on the basis of a graph indicating detection amounts of X-rays detected by the detection element arrays in the plurality of stages for the carrying direction.

With this configuration, an operator can easily designate one or more detection element arrays to be used for inspection on the basis of a determination result. One or more detection element arrays determined as being to be used for inspection can be automatically set as the detection element arrays to be used for the inspection.

Advantage of the Invention

The present invention can provide an X-ray inspection apparatus that can inspect an object to be inspected with high sensitivity by using a multiple-stage X-ray sensor without widening a slit of a collimator, and can prevent the apparatus from becoming large-sized due to prevention of X-ray leakage.

BEST MODE FOR CARRYING OUT THE INVENTION

Hereinafter, an embodiment of the present invention will be described with reference to the accompanying drawings.

An X-ray inspection apparatus of the present invention is incorporated into, for example, a part of a carrying line, irradiates an object to be inspected (product) sequentially carried from an upstream side with an X-ray, performs various inspections such as whether or not a foreign substance is contained, whether or not a seal part is defective, and whether or not there is a defective object on the basis of a transmission amount of the X-ray passing through the object to be inspected at that time, and carries out the object to be inspected to a downstream side.

Figure 1:
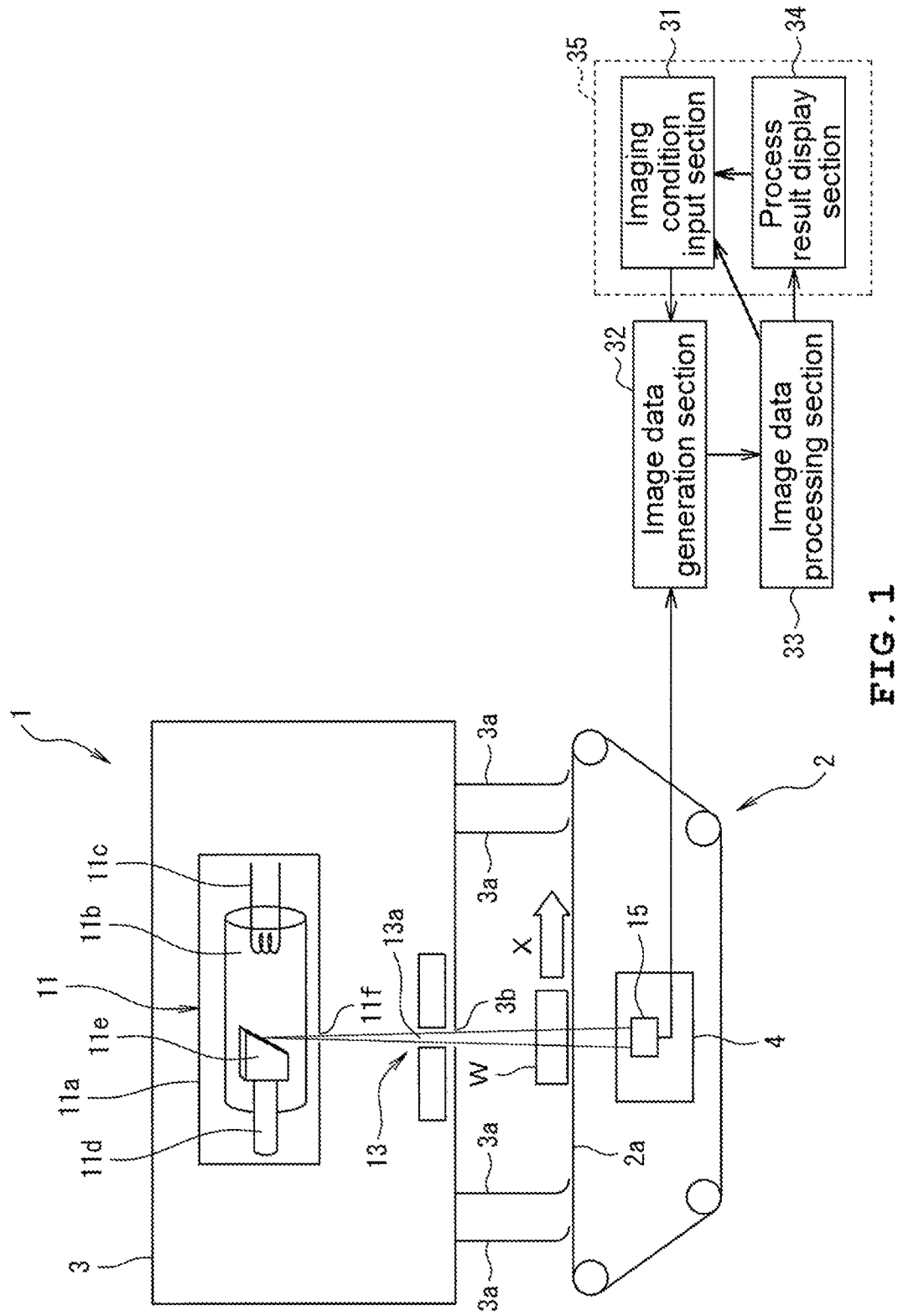
FIG. 1 is a configuration diagram schematically illustrating an X-ray inspection apparatus according to an embodiment of the present invention.

As illustrated in FIG. 1, an X-ray inspection apparatus 1 of the present embodiment includes a carrying section 2, a first unit 3, and a second unit 4.

The carrying section 2 is configured with a belt conveyor that is horizontally provided in, for example, an apparatus main body, and carries an object W to be inspected that is an inspection target onto a carrying path.

The carrying section 2 is provided with a carrying belt 2a made of a material (an element except elements having large atomic weights) through which an X-ray is easily transmitted, and drives the carrying belt 2a at a preset carrying speed due to rotation of a drive motor based on control of a carrying control portion (not illustrated) when the object W to be inspected is inspected. Consequently, the object W to be inspected that is carried from a carry-in port is carried toward a carry-out port in a carrying direction (a direction indicated by an arrow X).

The first unit 3 includes a casing configuring a unit on an X-ray irradiation side provided over the carrying path of the object W to be inspected, and an X-ray irradiation portion 11 and a collimator 13 are provided in the casing.

An irradiation aperture 3b through which an X-ray from the X-ray irradiation portion 11 is applied toward an X-ray sensor 15 which will be described later is formed on a casing bottom of the first unit 3. The irradiation aperture 3b is formed, for example, in a rectangular shape on a plane parallel to the carrying surface in a direction orthogonal to the carrying direction.

In the present embodiment, although not an essential configuration, shop-curtain type curtains 3a may be provided on the carry-in port side and the carry-out port side of the casing lower part of the first unit 3 such that an X-ray is relatively prevented from leaking to the outside.

The X-ray irradiation portion 11 irradiates, with an X-ray, the object W to be inspected carried on the carrying path in the carrying direction from the carry-in port toward the carry-out port, and generates the X-ray by hitting electrons accelerated due to application of a voltage against a target.

More specifically, the X-ray irradiation portion 11 has a configuration in which a cylindrical X-ray tube 11b provided in a metallic box body 11a having a rectangular parallelepiped shape is immersed in an insulating oil. The X-ray tube 11b is provided such that a longitudinal direction thereof is parallel to the carrying direction (or the direction orthogonal to the carrying direction) on a plane parallel to the carrying surface of the object W to be inspected.

In the X-ray tube 11b, a cathode 11c is disposed to face an anode target 11e supported at a support body 11d, and an electron beam from the cathode 11c is applied to the anode target 11e such that an X-ray is generated.

X-rays generated by the anode target 11e as an X-ray generation source are applied in a screen shape toward the X-ray sensor 15 which will be described later from an emission window 11f via the collimator 13. The emission window 11f is formed, for example, in a rectangular shape in the direction orthogonal to the carrying direction on a plane parallel to the carrying surface of the object W to be inspected.

The collimator 13 is provided to be located under the X-ray irradiation portion 11, and has, for example, a rectangular slit 13a restricting an X-ray irradiation region on the X-ray sensor 15 which will be described later, that is, the path of an X-ray applied toward the X-ray sensor 15 from the X-ray tube 11b.

The second unit 4 includes a casing configuring a unit on an X-ray detection side provided to face the first unit 3 and to be separated therefrom by a predetermined distance in a height direction on a lower carrying surface side of the object W to be inspected, and the X-ray sensor 15 is provided in the casing.

The X-ray sensor 15 includes a plurality of detection elements that are linearly arranged in the direction orthogonal to the carrying direction on a plane parallel to the carrying surface of the object W to be inspected.

The X-ray sensor 15 detects X-rays transmitted through the object W to be inspected and the carrying belt 2a with the plurality of detection elements, sequentially outputs detected data that is detected for each detection element with the number of the plurality of detection elements as one line, and repeats sequential output according to carrying of the object W to be inspected.

The output from the X-ray sensor 15 is used to perform various inspections such as whether or not a foreign substance is contained into the object W to be inspected, whether or not a seal part is defective, and whether or not there is a defective object. The X-ray sensor 15 faces the X-ray irradiation portion 11 with the carrying belt 2a interposed therebetween.

As an example, each detection element has a configuration in which a scintillator and a light receiving element such as a photodiode (not illustrated) are closely attached to each other, and converts an X-ray into light with the scintillator, converts the light into an electric signal with the light receiving element, and outputs the electric signal as X-ray transmission data.

As another example, each detection element may directly convert an X-ray into an electric signal with high efficiency according to a photon counting method by using a semiconductor such as cadmium telluride (CdTe).

At least one of the X-ray tube 11b, the collimator 13, and the X-ray sensor 15 is configured to be movable such that an X-ray irradiation region for the X-ray sensor 15 is adjustable.

Figure 2:
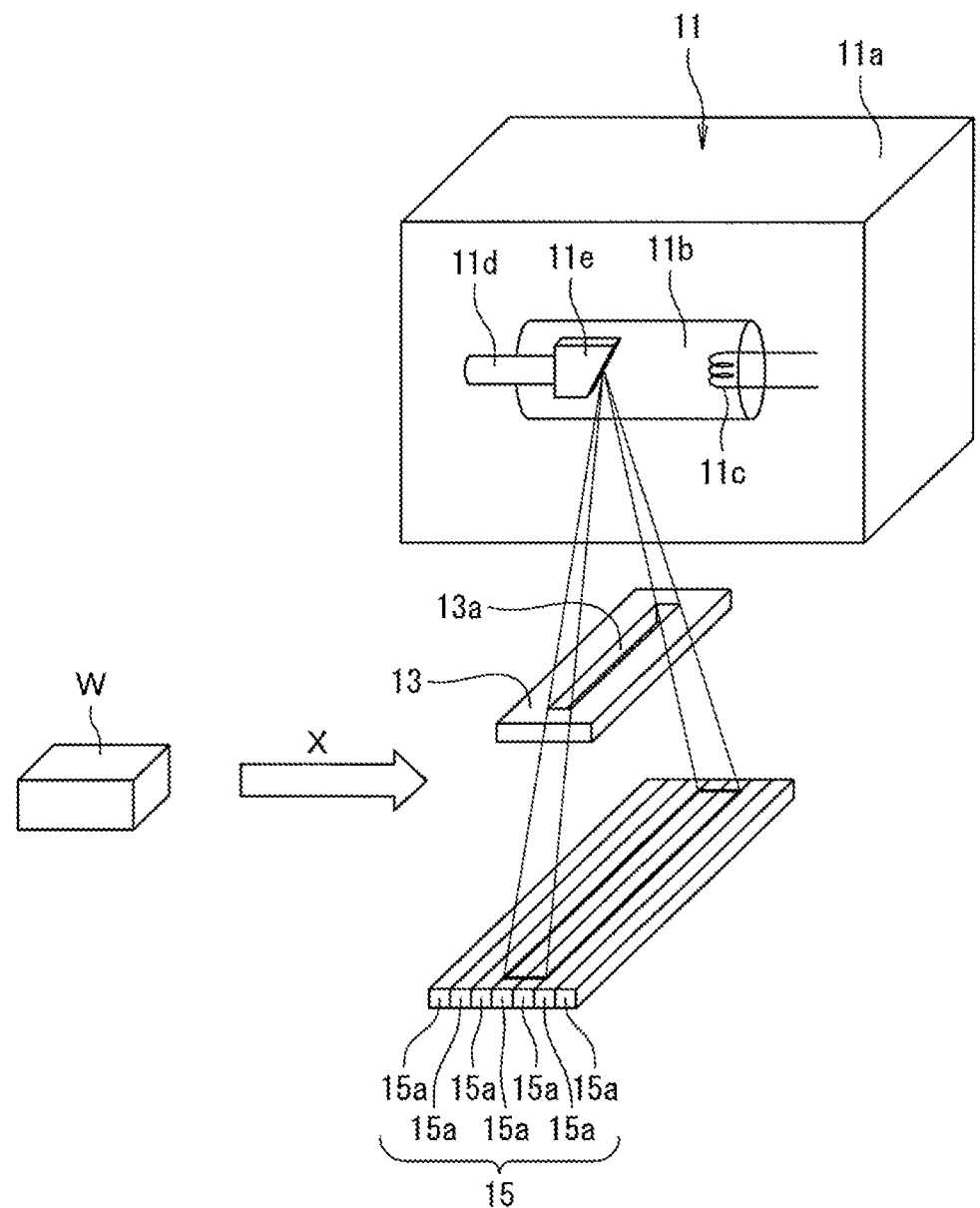
FIG. 2 is a perspective view illustrating configurations of a collimator and an X-ray sensor of the X-ray inspection apparatus according to the embodiment of the present invention.

As illustrated in FIG. 2, the X-ray sensor 15 includes detection element arrays 15a in a plurality of stages. Each of the detection element arrays 15a has a configuration in which a plurality of detection elements are linearly arranged in the direction orthogonal to the carrying direction on the plane parallel to the carrying surface of the object W to be inspected. The detection element arrays 15a are provided side by side in a plurality of stages (for example, 64 stages or 128 stages: only 7 stages are schematically illustrated in FIG. 2) along the carrying direction (X direction), and are thus formed in an array form.

As mentioned above, the X-ray sensor 15 is configured as a multiple-stage type X-ray sensor. As the multiple-stage type X-ray sensor, for example, a time delayed integration (TDI) type or TDS type X-ray sensor may be used.

The number of stages of the X-ray sensor 15 is not particularly limited as long as all of X-rays applied from the X-ray irradiation portion 11 via the collimator 13 can be detected in the number of stages.

Here, in the X-ray sensor 15 having the detection element arrays 15a in a plurality of stages as in the present embodiment, a size of the slit of the collimator 13 is made small, only the detection element arrays 15a in a portion irradiated with X-rays are used for inspection, and thus fine adjustment of an irradiation region for coping with a drift or the like of a focal position of the X-ray tube 11b is not necessary.

Only the detection element arrays 15a in a plurality of stages that detect X-rays with high efficiency in an irradiation region are used for inspection, and thus the object W to be inspected can be inspected with high sensitivity. To do so, it is necessary to specify the detection element arrays 15a to be used for inspection.

Therefore, as illustrated in FIG. 1, in the present embodiment, the X-ray inspection apparatus 1 includes an imaging condition input section 31 as a designation section. The imaging condition input section 31 is used for a user to designate a "use range" of the X-ray sensor 15. The use range indicates the detection element arrays 15a by which X-rays detected are used for inspection. In the present embodiment, the detection element arrays 15a that detect X-rays with high efficiency in an irradiation region restricted by the collimator 13 are designated as a use range. Here, the detection element arrays 15a that detect X-rays with high efficiency indicate the detection element arrays 15a in which irradiation states of X-rays are uniformly stable among the detection element arrays 15a in the irradiation region.

The X-ray inspection apparatus 1 includes a process result display section 34, and the process result display section 34 displays a detection amount of X-rays detected by the detection element arrays 15a in a plurality of stages. In the present embodiment, the process result display section 34 and the imaging condition input section 31 are integrated into a touch screen 35.

The imaging condition input section 31 is not limited to a touch screen, and may be configured with an input device such as a keyboard or a mouse. The display section 34 is not also limited to a touch screen, and may be configured with an output device such as a display or a projector.

The X-ray inspection apparatus 1 includes an image data processing section 33 as a determination section, and the image data processing section 33 generates a graph (a distribution of detection amounts) indicating detection amounts of X-rays in the carrying direction (X), detected by the detection element arrays 15a in a plurality of stages, and determines one or more detection element arrays to be used for inspection on the basis of the graph. Hereinafter, a range of the detection element arrays 15a to be used for inspection in the X-ray sensor 15 will be simply referred to as a "use range".

The image data processing section is configured with a general computer including a CPU and a memory, and a program operating on the CPU, and is not limited thereto, and may be configured with a dedicated device specialized for image processing instead of a general computer.

Figure 3:
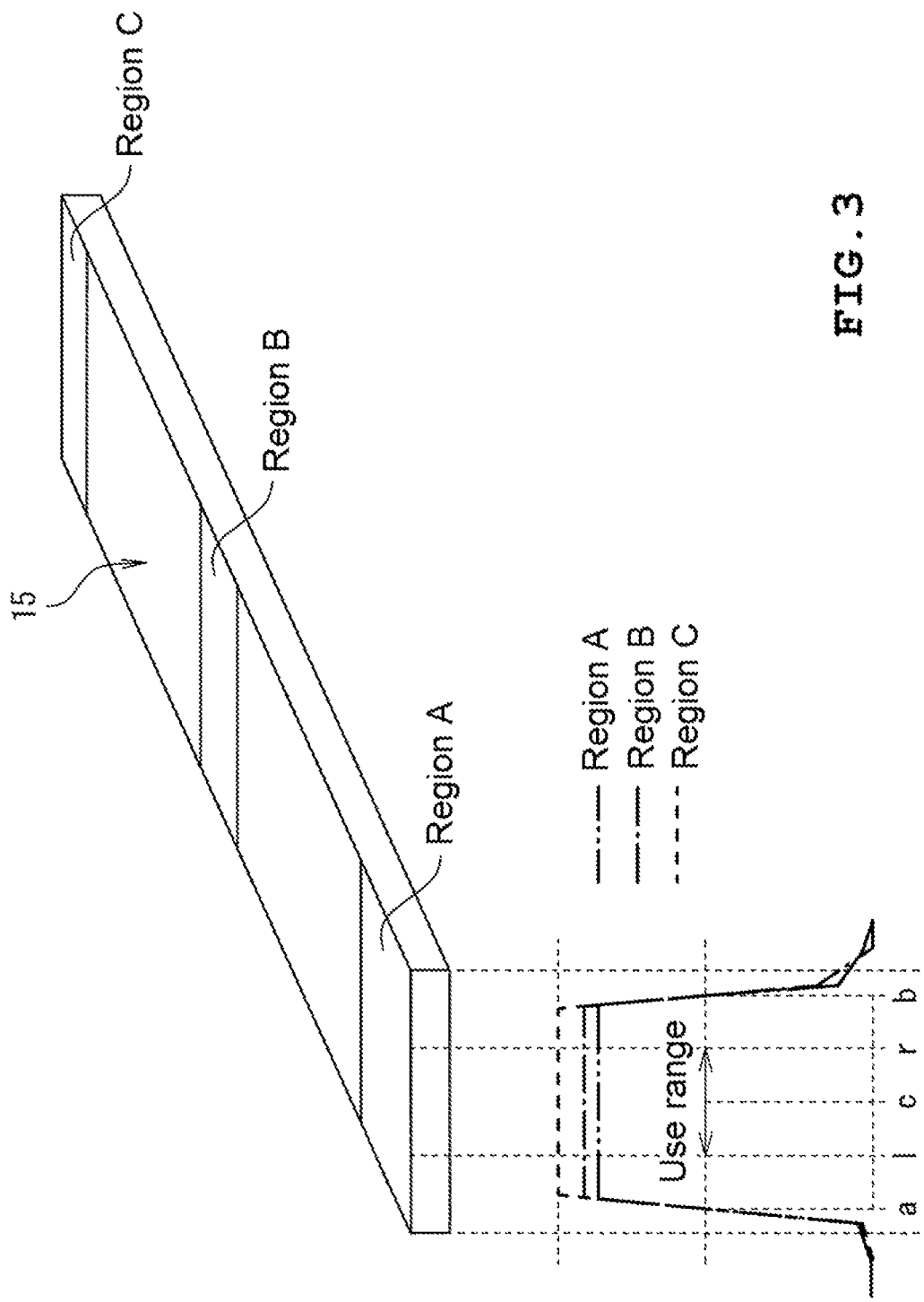
FIG. 3 is a diagram illustrating output from the X-ray sensor of the X-ray inspection apparatus according to the embodiment of the present invention.

Here, as a result of an X-ray irradiation region being restricted by the collimator 13, as indicated by graphs (line graphs) for X-ray detection amounts in regions A, B, and C of the X-ray sensor 15 illustrated in FIG. 3, an X-ray detection amount is the maximum in an X-ray irradiation region, and the X-ray detection amount is the minimum in a portion other than the irradiation region. The X-ray detection amount is inclined at end parts of the X-ray irradiation region.

Figure 4:
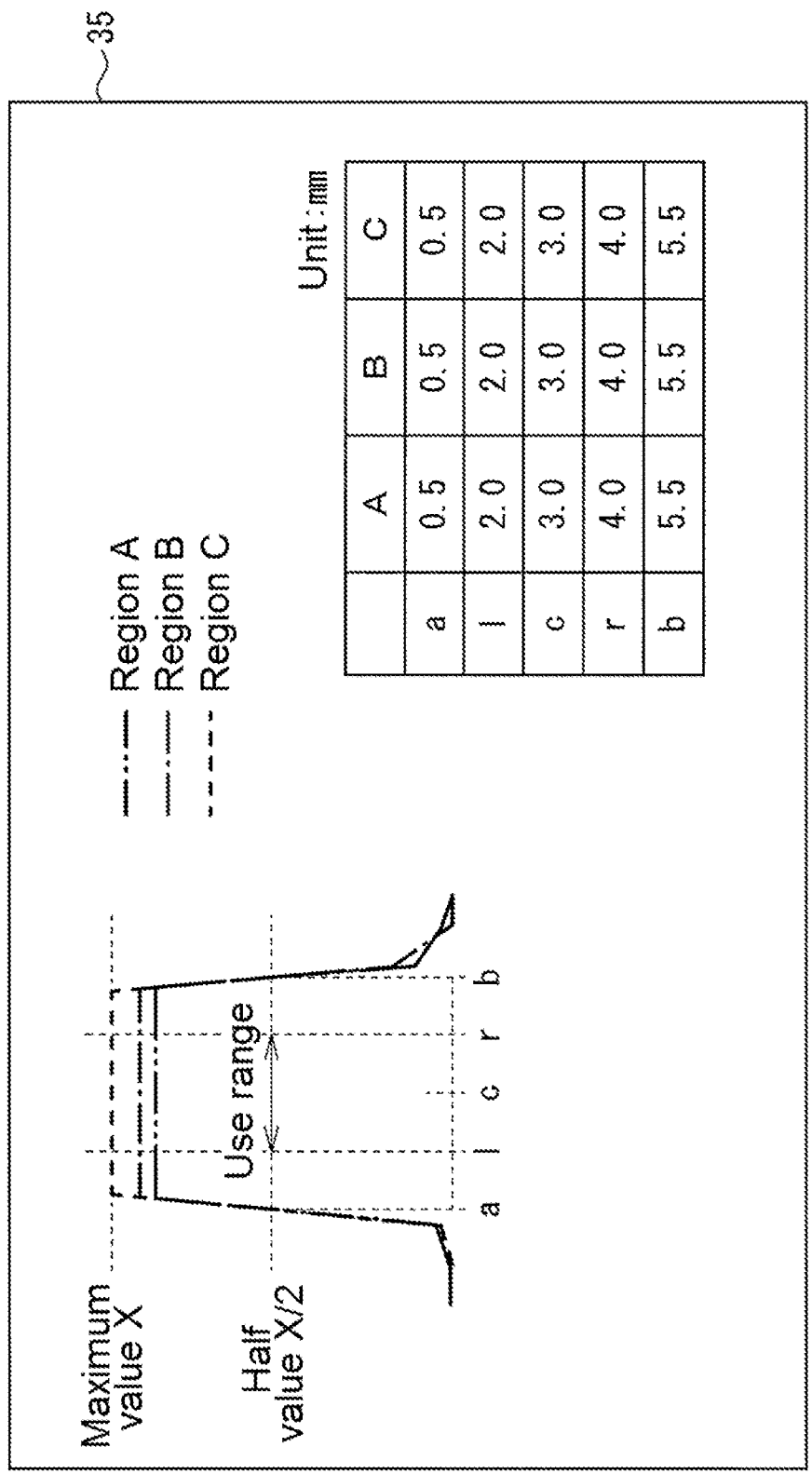
FIG. 4 is a diagram illustrating a screen display example in the X-ray inspection apparatus according to the embodiment of the present invention.

As illustrated in FIG. 4, the graphs for the regions A, B, and C, and distances [mm] to positions a, l, c, r, and b from a reference position on a transverse axis (X direction) of the graphs are displayed on a touch screen 35. The positions a and b are positions where an X-ray detection amount is a half value (X/2) of the maximum value (X) and the minimum value, and the position c is a middle position of the positions a and b.

The position l indicates a boundary of one end side of a region suitable as a use range, and is determined on the basis of the position c and the position a. The position r indicates a boundary of the other end side of a region suitable as the use range, and is determined on the basis of the position c and the position b.

In the present example, instead of the entire X-ray irradiation region, a range of only the detection element arrays 15a stably detecting X-rays with high efficiency in an irradiation region is set as a use range, that is, the detection element arrays 15a to be used as inspection such that the influence of a positional deviation or the like due to a temperature drift is not received.

The positions a, l, c, r, and b may be specified by using "numbers" (for example, TDI numbers) of the detection element arrays 15a instead of the "distances".

As described above, in the present embodiment, the X-ray inspection apparatus 1 includes the X-ray irradiation portion 11 having the X-ray tube 11b generating an X-ray, the X-ray sensor 15 having the detection element arrays 15a in a plurality of stages in the carrying direction, the detection element arrays 15a each formed of a plurality of detection elements linearly arranged in a main scanning direction orthogonal to the carrying direction on the plane parallel to the carrying surface of the object W to be inspected, and the collimator 13 restricting an X-ray irradiation region for the X-ray sensor 15.

The X-ray inspection apparatus 1 includes the imaging condition input section 31 as a designation section that designates the detection element arrays 15a detecting an X-ray with high efficiency in an irradiation region restricted by the collimator 13 as the detection element arrays 15a to be used for inspection.

With this configuration, an operator can designate the detection element array 15a detecting an X-ray with high efficiency in an irradiation region on the basis of, for example, a table for defining a correlation between a position of the collimator 13 and an X-ray irradiation region.

As a result, it is possible to inspect the object W to be inspected with high sensitivity with the multiple-stage X-ray sensor 15 without widening the slit 13a of the collimator 13, and to prevent the apparatus from becoming large-sized due to prevention of X-ray leakage.

In the present embodiment, the process result display section 34 as a display section displaying detection amounts of X-rays detected by the detection element arrays 15a in a plurality of stages is provided.

With this configuration, an operator can judge the one or more detection element arrays 15a detecting an X-ray with high efficiency by referring to the displayed X-ray detection amounts, and can thus designate the detection element arrays 15a as the detection element arrays 15a to be used for inspection.

In the present embodiment, there is provided the image data processing section 33 as a determination section determining one or more detection element arrays to be used for inspection on the basis of a graph (a distribution of a detection amount) indicating a detection amount of X-rays in the carrying direction (X), detected by the detection element arrays 15a in a plurality of stages.

With this configuration, an operator can easily designate the one or more detection element arrays 15a to be used for inspection on the basis of the detection element arrays 15a determined as being to be used for the inspection. The detection element arrays 15a determined as being to be used for inspection can be automatically set as the detection element arrays 15a to be used for the inspection.

As mentioned above, the preferable embodiment has been described, but the present invention is not limited by the techniques and the drawings according to the embodiment. In other words, needless to say, other embodiments, Examples, and operation techniques made by a person skilled in the art on the basis of the embodiment are all included in the category of the present invention.

DESCRIPTION OF REFERENCE NUMERALS AND SIGNS

1 X-ray inspection apparatus
11 X-ray irradiation portion
11b X-ray tube
13 Collimator
15 X-ray sensor
15a Detection element array
31 Imaging condition input section (designation section)
33 Image data processing section (determination section)
34 Process result display section (display section)
35 Touch screen
W Object to be inspected

What is claimed is:

1. An X-ray inspection apparatus that irradiates a carried object to be inspected with an X-ray, and inspects the object to be inspected on the basis of a transmission amount of the X-ray transmitted through the object to be inspected, the X-ray inspection apparatus comprising:
  an X-ray irradiation portion that has an X-ray tube generating the X-ray;
  an X-ray sensor that has detection element arrays in a plurality of stages in a carrying direction, the detection element arrays each formed of a plurality of detection elements linearly arranged in a main scanning direction orthogonal to the carrying direction on a plane parallel to a carrying surface of the object to be inspected and detecting the X-ray;
  a collimator that restricts an irradiation region of the X-ray for the X-ray sensor; and
  at least one processor configured to designate one or more detection element arrays to be used for inspection in the irradiation region restricted by the collimator.

2. The X-ray inspection apparatus according to claim 1, further comprising:
  a display that displays a detection amount of X-rays detected by the detection element arrays in the plurality of stages.

3. The X-ray inspection apparatus according to claim 1, wherein the at least one processor is further configured to determine the one or more detection element arrays to be used for the inspection on the basis of a graph indicating detection amounts of X-rays detected by the detection element arrays in the plurality of stages for the carrying direction.

* * * * *